United States Patent
Grab

(10) Patent No.: US 9,415,032 B2
(45) Date of Patent: Aug. 16, 2016

(54) MEMBRANE ACTIVATED CHELATORS AND USE IN THE PREVENTION AND TREATMENT OF PARASITIC INFECTION

(71) Applicant: THE JOHNS HOPKINS UNIVERSITY, Baltimore, MD (US)

(72) Inventor: Dennis John Grab, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 157 days.

(21) Appl. No.: 14/349,677

(22) PCT Filed: Oct. 5, 2012

(86) PCT No.: PCT/US2012/058932
§ 371 (c)(1),
(2) Date: Apr. 4, 2014

(87) PCT Pub. No.: WO2013/052787
PCT Pub. Date: Apr. 11, 2013

(65) Prior Publication Data
US 2014/0303247 A1  Oct. 9, 2014

Related U.S. Application Data

(60) Provisional application No. 61/543,564, filed on Oct. 5, 2011, provisional application No. 61/543,575, filed on Oct. 5, 2011.

(51) Int. Cl.
*A61K 31/09* (2006.01)
*A61K 31/132* (2006.01)
*A61K 31/135* (2006.01)
*A61K 31/192* (2006.01)
*A61K 31/194* (2006.01)
*A61K 31/216* (2006.01)
*A61K 31/197* (2006.01)
*A61K 45/06* (2006.01)
*C07C 229/42* (2006.01)

(52) U.S. Cl.
CPC .............. *A61K 31/216* (2013.01); *A61K 31/09* (2013.01); *A61K 31/132* (2013.01); *A61K 31/135* (2013.01); *A61K 31/192* (2013.01); *A61K 31/194* (2013.01); *A61K 31/197* (2013.01); *A61K 45/06* (2013.01); *C07C 229/42* (2013.01)

(58) Field of Classification Search
CPC ... A61K 31/09; A61K 31/132; A61K 31/135; A61K 31/192; A61K 31/194; A61K 31/216
See application file for complete search history.

(56) References Cited

U.S. PATENT DOCUMENTS

2002/0102570 A1  8/2002  Baker
2006/0167092 A1  7/2006  Striem et al.

FOREIGN PATENT DOCUMENTS

EP  1027325 B1  3/2003
WO  2007-136626 A1  11/2007

OTHER PUBLICATIONS

Rosenberg, G., et al., "The membrane-activated chelator stroke intervention (MACSI) trial of DP-b99 in acute ischemic stroke: a randomized double-blind, placebo-controlled, multinational pivotal Phase III study", International Journal of Stroke, Aug. 2011, vol. 6, pp. 362-367.

*Primary Examiner* — Yong Chong
(74) *Attorney, Agent, or Firm* — Johns Hopkins Technology Transfer

(57) ABSTRACT

Provided herein are pharmaceutical compositions useful in the prevention and treatment of protozoan infections in mammals comprising administering to the subject a pharmaceutical composition comprising at least one membrane activated chelator compound which is a lipophilic diester derivative of the chelating agent 1,2-bis(2 aminophenoxy)ethane-N,N,N',N'-tetraacetic acid, or a salt, solvate, stereoisomer, or prodrug thereof, as well as compositions which include at least one or more other anti-parasitic compound, and a pharmaceutically acceptable carrier, in an effective amount. Methods for prevention, treatment, and combination therapies are also provided.

9 Claims, 3 Drawing Sheets

MEMBRANE ACTIVATED CHELATORS AND USE IN THE PREVENTION AND TREATMENT OF PARASITIC INFECTION

CROSS-REFERENCE TO RELATED APPLICATIONS

This application is a 35 U.S.C. 371 U.S. national entry of International Application PCT/US2012/058932, having an international filing date of Oct. 5, 2012, which claims the benefit of U.S. Provisional Application Nos. 61/543,564, and 61/543,575, both filed on Oct. 5, 2011, the content of each of the aforementioned applications are herein incorporated by reference for all purposes as if fully set forth herein.

BACKGROUND OF THE INVENTION

Human African trypanosomiasis (HAT), also known as sleeping sickness, is a vector-borne parasitic disease. The parasites concerned are protozoa belonging to the *Trypanosoma* genus, such as (*Trypanosoma brucei rhodesiense* (Tbr) or *Trypanosoma brucei gambiense* (Tbg). They are transmitted to humans by tsetse fly (*Glossina* genus) bites which have acquired their infection from human beings or from animals harbouring the human pathogenic parasites.

In the first stage, the trypanosomes multiply in subcutaneous tissues, blood and lymph. This is known as a haemolymphatic phase, which entails bouts of fever, headaches, joint pains and itching.

In the second stage the parasites cross the blood-brain barrier to infect the central nervous system. This is known as the neurological phase. In general this is when more obvious signs and symptoms of the disease appear: changes of behavior, confusion, sensory disturbances and poor coordination. Disturbance of the sleep cycle, which gives the disease its name, is an important feature of the second stage of the disease. Without treatment, sleeping sickness is considered fatal.

Malaria is another one of most dangerous infectious diseases in tropical and subtropical countries, afflicting about 300 million people. The pathogen of the disease is a protozoan parasite, *Plasmodium* sp. which is transmitted by Anopheles mosquitoes. Four species of malaria parasites can infect humans under natural conditions: *Plasmodium falciparum, P. vivax, P. ovale,* and *P. malariae. P. falciparum* and *P. vivax* cause the most infections worldwide. *P. falciparum* is the agent of severe, potentially fatal malaria. Malaria caused by *P. falciparum* is responsible for nearly 1 million deaths annually. Based on recent estimates from the WHO, worldwide, there were an estimated 247 million malaria cases among 3.3 billion people at risk living in 109 countries. Infections caused by *P. falciparum* and *P. vivax* account for more than 90% of global malaria burden; the former being responsible for nearly all the deaths due to malaria, nearly a million deaths of children under 5 years.

Membrane activated chelators (MACs) are neuroprotective drugs that modulate cell membrane metal ion homeostasis by adopting an inactive conformation outside only in the lipid environment of cell membranes. In this environment, the drugs are able to unable to bind metal ions at their elevated non-physiological concentrations, which results in a drug with excellent tolerability. See, for example U.S. Pat. Nos. 6,458,837 and 7,799,831, incorporated by reference herein. DP-b99, a BAPTA-based lipophilic MAC of calcium, zinc and copper has been safely used in humans and is currently in phase III clinical trials for treatment of acute ischemic stroke. The safety, tolerability, and efficacy of related compounds DP-109 and DP-460 has also been demonstrated as these compounds have shown promise in mouse models of Alzheimer's disease and amyotrophic lateral sclerosis There still exists a need for more effective chemotherapeutic treatments for parasitic diseases such as HAT and malaria, around the world.

SUMMARY OF THE INVENTION

While it was known that *T. brucei* contains $Ca^{2-}$-binding proteins such as calmodulin (CaM) and other EF-hand proteins (IFHS, Tb17, Tb24, Tb44) and PKC-like activity, and that very large $Ca^{2+}$ reservoirs are also maintained in the acidocalcisome, a unique organelle, which also contains $Zn^{2+}$. The inventors hypothesized that by chelating parasite $Ca^{2+}$ and $Zn^{2+}$ using MACs might modulate their growth and/or be anti-parasitical.

In accordance with an embodiment, the present invention provides a pharmaceutical composition comprising at least one membrane activated chelator compound of formula I:

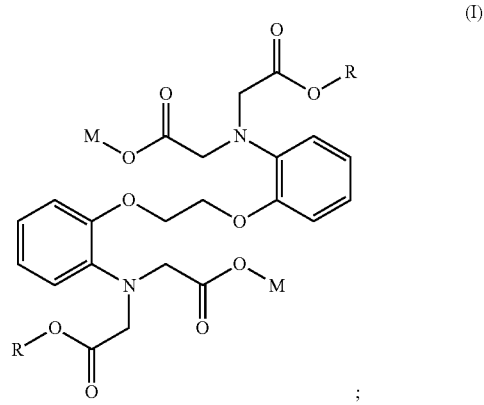

(I)

or a salt, solvate, stereoisomer, or prodrug thereof, wherein R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and M denotes a hydrogen or a physiologically acceptable cation, and a pharmaceutically acceptable carrier, in an amount effective for use as a medicament, and preferably for use in the prevention and/or treatment of a parasitic infection in a subject.

In accordance with another embodiment, the present invention provides a method for treatment of a parasitic infection in a subject, comprising administering to the subject a pharmaceutical composition comprising at least one membrane activated chelator compound of formula I:

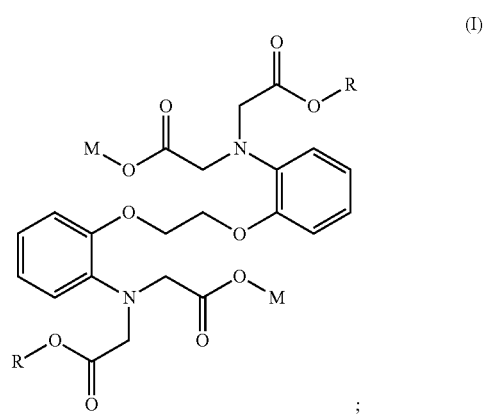

(I)

or a salt, solvate, stereoisomer, or prodrug thereof, wherein R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and M denotes a hydrogen or a physiologically acceptable cation, and a pharmaceutically acceptable carrier, in an effective amount.

In accordance with a further embodiment, the present invention provides a method for treatment of a parasitic infection in a subject, comprising administering to the subject a pharmaceutical composition comprising at least one membrane activated chelator compound of formula I:

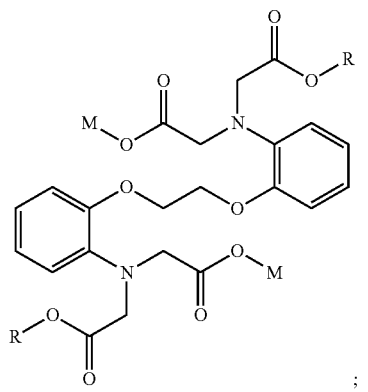

(I)

or a salt, solvate, stereoisomer, or prodrug thereof, wherein R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and M denotes a hydrogen or a physiologically acceptable cation, at least one or more other anti-parasitic compound, and a pharmaceutically acceptable carrier, in an effective amount.

DETAILED DESCRIPTION OF THE INVENTION

Figure 1:
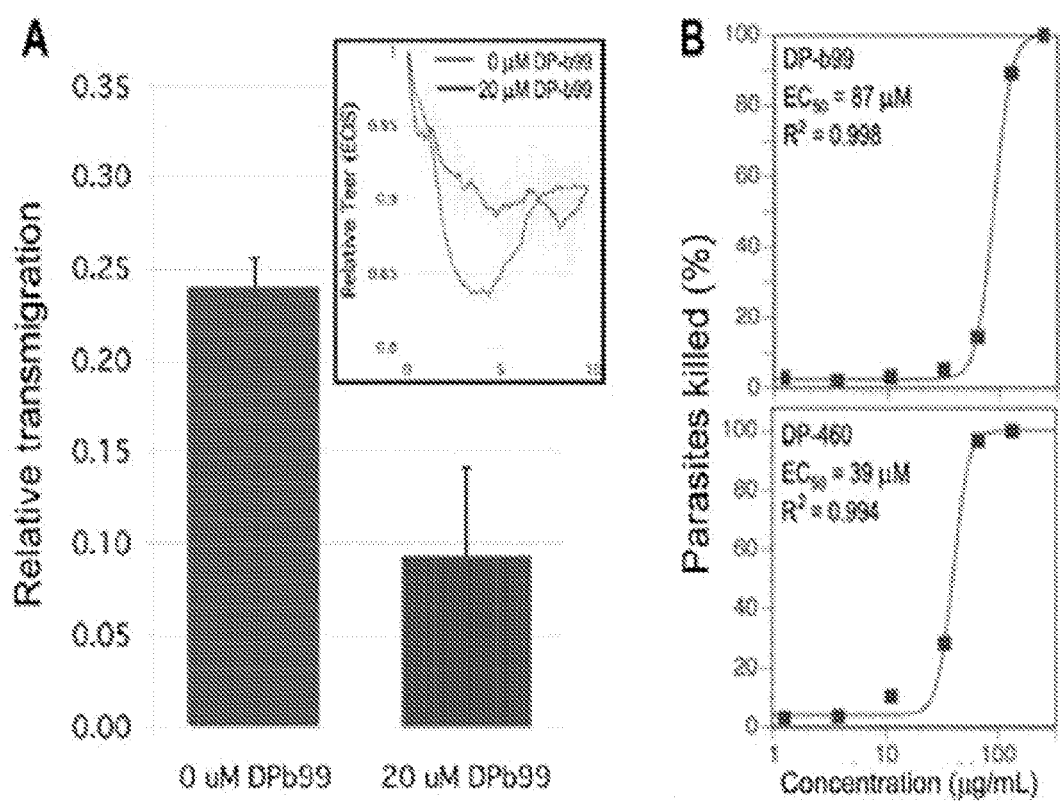
FIG. 1 illustrates the effect of MACs of the present invention on human brain microvascular endothelial cell (BMEC) monolayers interaction with trypanosomes. (A) Human BMEC pretreated with 20 µM DP-b99 impeded parasite transmigration across this barrier (t-5 hours, n=3). Human BMEC also maintained a tighter barrier during the infection as measured by grown on gold-coated electrode electric cell-substrate impedance sensing (ECIS) transendothelial electrical resistance (TEER) arrays (insert). The data are represented as average TEER or migration±S.E. (n=4; p<0.05). (B) BSF trypanosomes were incubated with DP-b99 or DP460. The average percent (n=4) of parasites killed after 24 hours is plotted against drug concentration.
Figure 2:
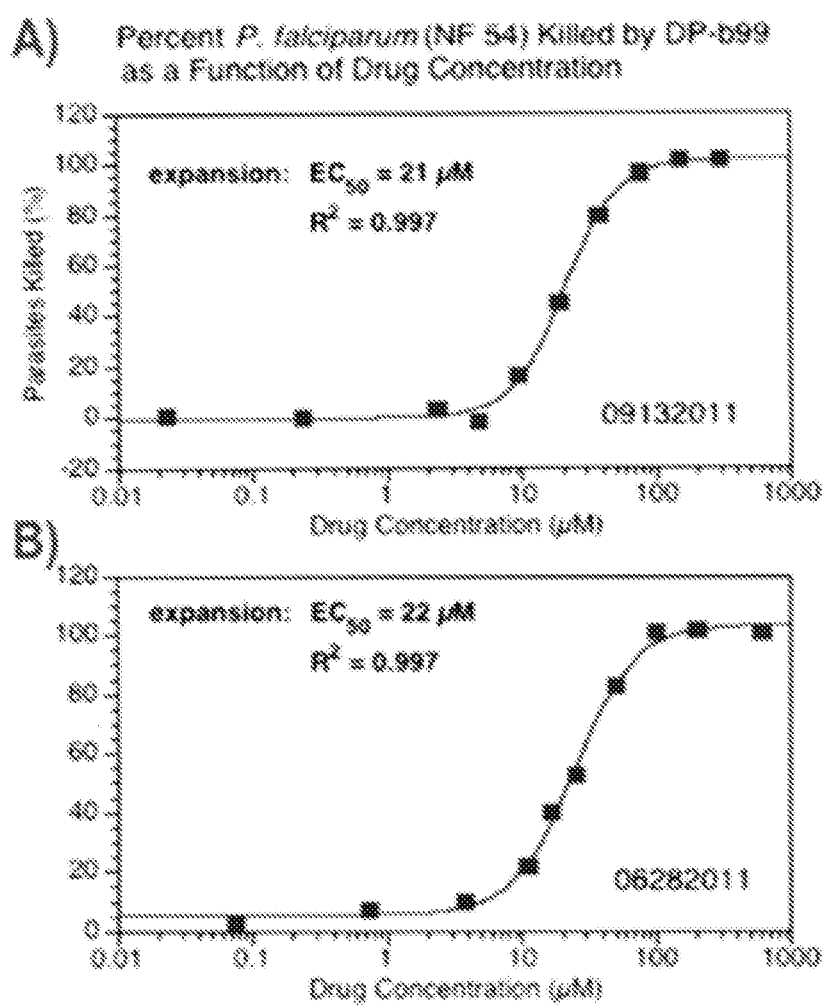
FIG. 2 is set of graphs showing the percentage of *P. falciparum* killed by MACs of the present invention as a function of drug concentration. Malaria-infected RBC were incubated with DP-b99 (A and B).
Figure 3:
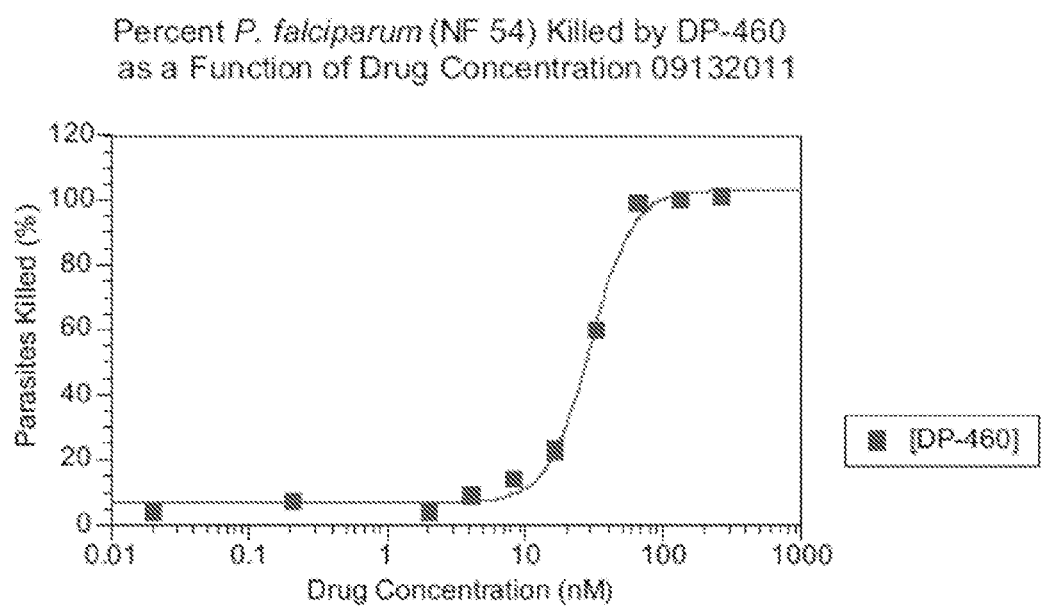
FIG. 3 is a graph showing the percentage of *P. falciparum* killed by MACs of the present invention as a function of drug concentration. Malaria-infected RBC were incubated with DP-460 with an $EC_{50}$ of 28 µM and $R^2$=0.995.

In accordance with an embodiment, the present invention provides a pharmaceutical composition comprising at least one membrane activated chelator compound of formula I:

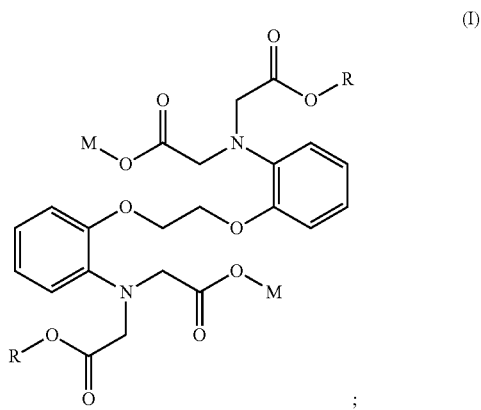

(I)

or a salt, solvate, stereoisomer, or prodrug thereof, wherein R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and M denotes a hydrogen or a physiologically acceptable cation, and a pharmaceutically acceptable carrier, in an amount effective for use as a medicament, and preferably for use in the prevention and/or treatment of a parasitic infection in a subject.

As used herein, examples of the term "alkyl" preferably include a $C_{1-6}$ alkyl (e.g., methyl, ethyl, propyl, isopropyl, butyl, isobutyl, sec-butyl, tert-butyl, pentyl, hexyl, etc.) and the like.

As used herein, examples of the term "alkenyl" preferably include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

As used herein, examples of the term "alkynyl" preferably include $C_{2-6}$ alkynyl (e.g., ethynyl, propargyl, 1-butynyl, 2-butynyl, 3-butynyl, 1-hexynyl, etc.) and the like.

Examples of the term "cycloalkyl" preferably include a $C_{3-8}$ cycloalkyl (e.g., a cyclopropyl, cyclobutyl, cyclopentyl, cyclohexyl, etc.) and the like.

Examples of the term "aryl" preferably include a $C_{6-14}$ aryl (e.g., a phenyl, 1-naphthyl, a 2-naphthyl, 2-biphenylyl group, 3-biphenylyl, 4-biphenylyl, 2-anthracenyl, etc.) and the like.

Examples of the term "arylalkyl" preferably include a $C_{6-14}$ arylalkyl (e.g., benzyl, phenylethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The terms "alkylthio," "alkenylthio" and "alkynylthio" mean a group consisting of a sulphur atom bonded to an alkyl-, alkenyl- or alkynyl-group, which is bonded via the sulphur atom to the entity to which the group is bonded.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

In accordance with an embodiment, the present invention also provides methods utilizing the pharmaceutical compositions described above, wherein R in the compound of Formula (I) is a phenylalkyl, and alky interrupted by zero to three oxygen atoms, or a monoalkyl ether of mono-, di, or tri-ethylene glycol.

In accordance with another embodiment, the present invention provides methods utilizing the pharmaceutical compositions described above, wherein R in the compound of Formula (I) is selected from the group consisting of: $C_8H_{17}$, $C_8H_{17}OCH_2CH_2$, $C_{18}H_{37}$, $C_{18}H_{37}OCH_2CH_2$, benzyl-$CH_2OCH_2CH_2$, $C_{12}H_{25}OCH_2CH_2$, $C_{12}H_{25}(OCH_2CH_2)_2$ and $C_{12}H_{25}(OCH_2CH_2)_3$.

In accordance with another embodiment, the present invention provides methods utilizing the pharmaceutical compositions described above, wherein said compound of Formula (I) is selected from the group consisting of: 1,2-bis(2-aminophenoxy)ethane, N,N'-di(2-octoxyethyl acetate), N,N'-diacetic acid; 1,2-bis(2-aminophenoxy)ethane, N,N'-di(2-octodecyloxyethyl acetate), N,N'-diacetic acid; 1,2-bis(2-aminophenoxy)ethane, N,N'-di(2-benzyloxyethyl acetate), N,N'-acetic acid; 1,2-bis(2-aminophenoxy)ethane, N,N'-di(2-dodecyloxyethyl acetate), N,N'-diacetic acid; 1,2-bis(2-aminophenoxy)ethane, N,N'-di[2-(2-dodecyloxyethoxy)-ethyl acetate], N,N'-diacetic acid; and 1,2-bis(2-aminophenoxy)ethane, N,N'-di{2-[2-(2-dodecyloxyethoxy)ethoxy]-ethyl acetate}, N,N'-diacetic acid.

In accordance with another embodiment, the present invention provides methods utilizing the pharmaceutical compositions described above, wherein the compound is selected from the group consisting of:

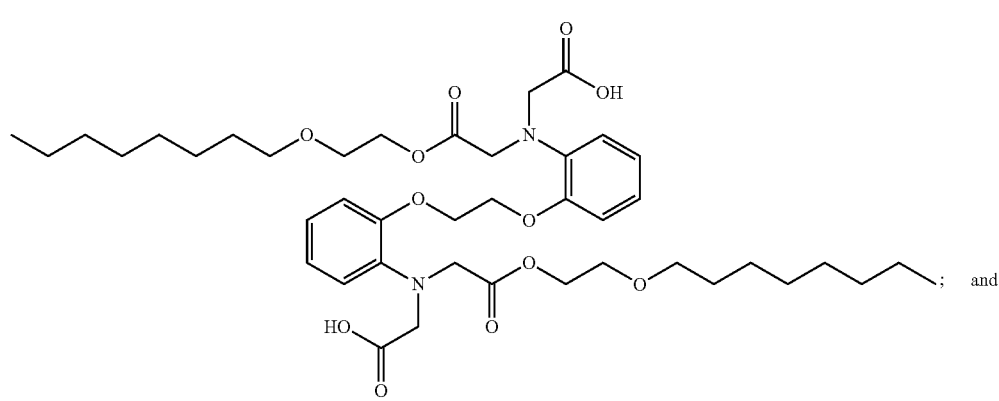

(DP-b99)

; and (DP-460)

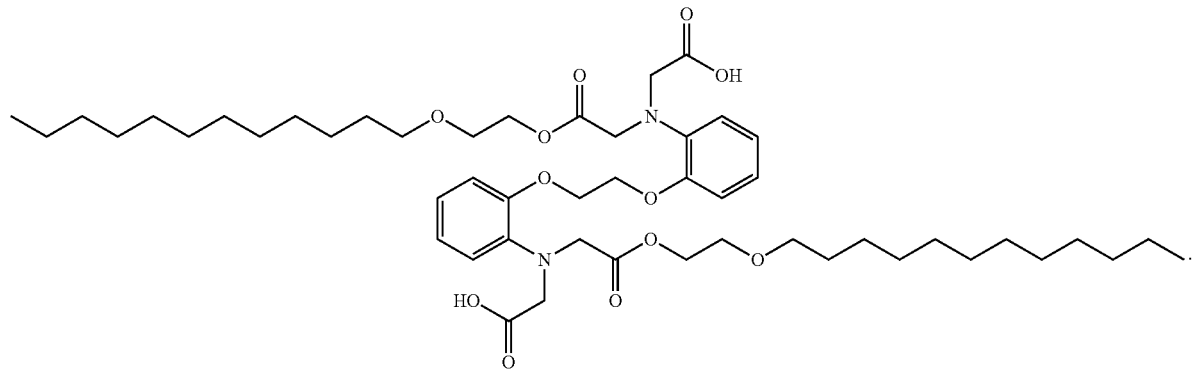

In accordance with one or more embodiments, the present invention provides methods utilizing the pharmaceutical compositions described above wherein the parasitic infection is caused by infection of the subject with a protozoan organism. Examples of protozoan organisms treated by the pharmaceutical compositions and methods described herein include, but are not limited to *Acanthamoeba, Babesia, Balantidium, Cryptosporidium, Dientamoeba, Entamoeba, Giardia, Isospora, Leishmania, Naegleria, Plasmodium, Sarcocystis, Toxoplasma, Trichomonas*, and *Trypanosoma*.

In accordance with an embodiment, the present invention provides a method for treatment of a parasitic infection in a subject, comprising administering to the subject a pharmaceutical composition comprising at least one membrane activated chelator compound of formula I:

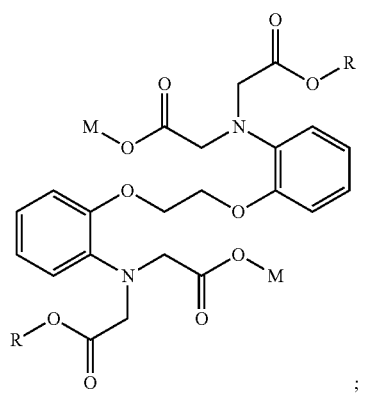

or a salt, solvate, stereoisomer, or prodrug thereof, wherein R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and M denotes a hydrogen or a physiologically acceptable cation, and a pharmaceutically acceptable carrier, in an effective amount.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In accordance with an embodiment, the present invention provides methods of preventing or treating infection in a subject, wherein the infection is caused by the protozoan organisms *Trypanosoma brucei rhodesiense* (Tbr) or *Plasmodium falciparum*.

In accordance with an embodiment, the present invention provides a method for treatment of a parasitic infection in a subject, comprising administering to the subject a pharmaceutical composition comprising at least one membrane activated chelator compound of formula I:

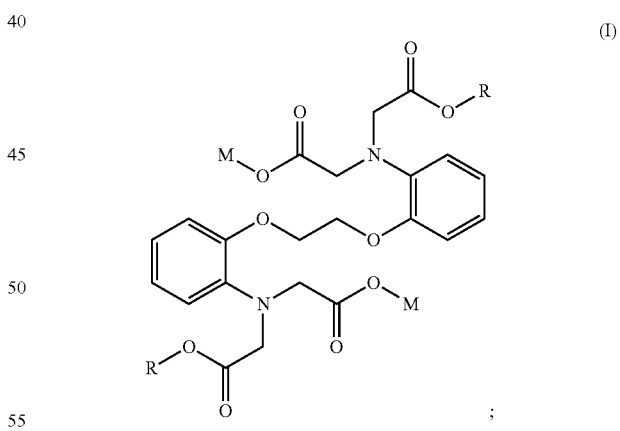

or a salt, solvate, stereoisomer, or prodrug thereof, wherein R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and M denotes a hydrogen or a physiologically acceptable cation, at least one or more other anti-parasitic compound, and a pharmaceutically acceptable carrier, in an effective amount.

In accordance with another embodiment, the present invention provides methods utilizing the pharmaceutical compositions described above and at least one or more other anti-parasitic compounds.

As used herein, the term "anti-parasitic compound" means one or more active agents from the class of drugs known as antiprotozoals, anthelmintics, ectoparasiticides, and similar compounds. These groups include antiamebiasis agents, antifascioliasis agents, antifiliariasis agents, antileshmaniasis agents, antimalarials, antischistosomal agents, antitapeworm agents and antitrypanosomiasis agents. Examples of such compounds include ornithine, arsenicals, benzamidine, napthalenesulfonate, nitroimidazole, macrolides, nitrofuran, pentavalent anitmonials, phosphoryl choline, neomycin, thiazole, aminoacridine, oxyquinoline, tetracycline, trimethoprim/sulfamethoxazole, pyirmethamine, aminoquinolines, 4-methanolquinolines, biguanides, sulfonamides, sesquiterpene lactones, atovaquone, pyronaridine, piperaquine, artesunate-amodiaquine, nitroimidazole derivatives, Ivermectin, and related compounds. Also included in the term "anti-parasitic compounds" are vaccines and antibodies to infectious parasites.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physicochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flowaids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds, salts, solvates, or stereoisomers of any one the compounds of Formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds of Formula I, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, about 0.1 mg to about 10 mg/kg body weight/day.

Alternatively, the compounds of the present invention can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous or non-porous material, such as a polymer, wherein the compound is encapsulated by or diffused throughout the material and/or degradation of the non-porous material. The depot is then implanted into the desired location within the body and the compounds are released from the implant at a predetermined rate.

In one embodiment, the compounds of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all, or substantially all of the compound, is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds included in the pharmaceutical compositions of the present invention may also include incorporation of the active ingredients into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present invention, the compounds of the present invention may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently, or in lower doses than with the unmodified compound.

EXAMPLE 1

African Trypanosomes: The MAC compound of the present invention, DP-b99, as a chelator of $Ca^{2+}$ and $Zn^{2+}$ was tested to determine whether it would tighten the BBB to trypanosome traversal based on the concepts described above. In pilot parasite/BBB transmigration experiments, bloodstream form *Trypanosoma brucei rhodesiense* (Tbr) IL1852 were incubated in Transwell inserts containing human brain microvascular endothelial cell (BMEC) monolayers pretreated for 60 minutes with DP-b99, then washed free of drug. In a parallel experiment, human BMEC grown on gold-coated electrode ECIS arrays, were similarly treated with the MAC compound. When compared to the untreated control group, *T. b. rhodesiense* transmigration across a human BMEC barrier was impeded 60% after 5 hours incubation (FIG. 1A). The 5 hour time point was chosen based on the maximal negative change in real-time TEER using ECIS (FIG. 1A, insert) in the parallel experiment. We were surprised to find that DP-b99 had trypanocidal properties in vitro using a well validated cytotoxicity assay for trypanosome drug testing (J. Infect. Dis., 1995; 172(4):1157-9). The effective concentration of drug to kill 50% ($EC_{50}$) of the parasites (*T. b. brucei* 427 or *T. b. rhodesiense* IL1852) by 24 hours was about 87 μM for DP-b99 and 39 μM for DP-460 (FIG. 1B). These in vitro data show that MAC compounds will both kill trypanosomes and impede parasite brain entry. Considering their general neuroprotective properties, it is thought that that MAC compounds of the present invention will also prevent or minimize melarsoprol induced post-treatment reactive encephalopathy (PTRE). Current pilot studies show that MACs also have antitrypanocidal properties in vivo (mice) (data not shown).

EXAMPLE 2

Malaria. Because of the importance of calcium signaling in mammalian cells and recent findings that interference with host cell signaling pathways to subvert the host intracellular milieu may be an important mechanism for the malaria parasite's survival, it was thought that MACs might be toxic to malarial parasite within host cells (i.e. RBCs, hepatocytes). It was investigated whether MAC compounds of the present invention would be able to kill intracellular malaria parasites. An established antimalarial cytotoxicity assay developed in Dr. Theresa Shapiro's laboratory (JHU) (Tetrahedron, 1997; 53(1):37-50) was used with the following modifications: (1) Parasitemia was maintained at 0.1% to 5% by thrice weekly change of medium and replenishment of human erythrocytes; (2) [$^3$H]hypoxanthine (10-30 Ci/mmol, 1.0 mCi/mL was used in aqueous solution, (Perkin-Elmer NET177001MC), diluted to 25 μCi/mL with medium; and as for the trypanosome experiments (3) the cytotoxicity assays for two MAC compounds of the present invention, DP-b99 and DP-460 (DP-harm, Ltd., Rehovot Ill.), included 10 concentrations based on stock solutions (50.0 mg/mL) of each compound that were prepared in sterile HPLC-grade water. In pilot experiments, both DP-b99 (FIGS. 2A, B) and DP-460 (FIG. 3) were found to kill *P. falciparum* in the 21-28 μM range.

These data show that MAC compounds of the present invention will both kill African trypanosomes, malaria and possible other medically important protozoan parasites (i.e. *Leishmania, T. cruzi*), and are important to the disease process (i.e HAT) impede parasite brain entry. These findings, are (trypanosomes) or (malaria) now being tested in appropriate in vivo rodent models.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treatment of a parasitic infection in a subject, comprising administering to the subject a pharmaceutical composition comprising at least one membrane activated chelator compound of formula I:

(I)

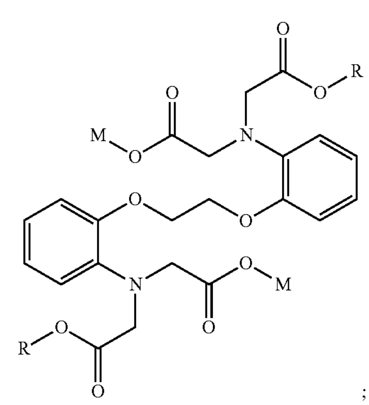

;

or a salt, solvate, stereoisomer, or prodrug thereof, wherein R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and M denotes a hydrogen or a physiologically acceptable cation, and a pharmaceutically acceptable carrier, in an amount effective to suppress or eliminate the parasite from the subject, wherein the parasitic infection is caused by infection of the subject with a protozoan organism selected from the group consisting of: *Acanthamoeba, Babesia, Balantidium, Cryptosporidium, Dientamoeba, Entamoeba, Giardia, Isospora, Leishmania, Naegleria, Plasmodium, Sarcocystis, Toxoplasma, Trichomonas*, and *Trypanosoma*.

2. The method of claim 1, wherein the protozoan organism is *Trypanosoma brucei rhodesiense* (Tbr).

3. The method of claim 1, wherein the protozoan organism is *Plasmodium falciparum*.

4. The method of claim 1, wherein R in the compound of Formula (I) is a phenylalkyl, and alkyl interrupted by zero to three oxygen atoms.

5. The method of claim 1, wherein R in the compound of Formula (I) is a monoalkyl ether of mono-, di, or tri-ethylene glycol.

6. The method of claim 1, wherein, wherein R in the compound of Formula (I) is selected from the group consisting of: $C_8H_{17}$, $C_8H_{17}OCH_2CH_2$, $C_{18}H_{37}$, $C_{18}H_{37}OCH_2CH_2$, benzyl-$CH_2OCH_2CH_2$, $C_{12}H_{25}OCH_2CH_2$, $C_{12}H_{25}(OCH_2CH_2)_2$ and $C_{12}H_{25}(OCH_2CH_2)_3$.

7. The method of claim 6, wherein said compound of Formula (I) is selected from the group consisting of: 1,2-bis(2-aminophenoxy)ethane, N,N'-di(2-octoxyethyl acetate), N,N'-diacetic acid; 1,2-bis(2-aminophenoxy)ethane, N,N'-di(2-octodecyloxyethyl acetate), N,N'-diacetic acid; 1,2-bis(2-aminophenoxy)ethane, N,N'-di(2-benzyloxyethyl acetate), N,N'-acetic acid; 1,2-bis(2-aminophenoxy)ethane, N,N'-di(2-dodecyloxyethyl acetate), N,N'-diacetic acid; 1,2-bis(2-aminophenoxy)ethane, N,N'-di[2-(2-dodecyloxyethoxy)-ethyl acetate], N,N'-diacetic acid; and 1,2-bis(2-aminophenoxy)ethane, N,N'-di {2-[2-(2-dodecyloxyethoxy) ethoxy]-ethyl acetate}, N,N'-diacetic acid.

8. The method of claim 7, wherein the compound is selected from the group consisting of:

(DP-b99)

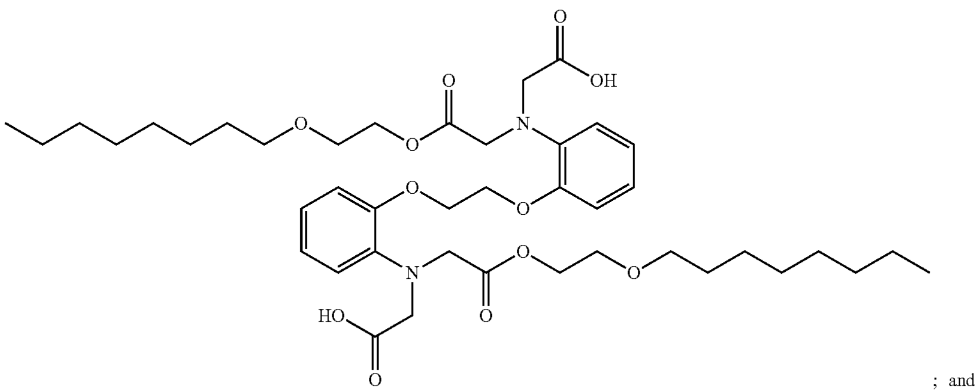

; and (DP-460)

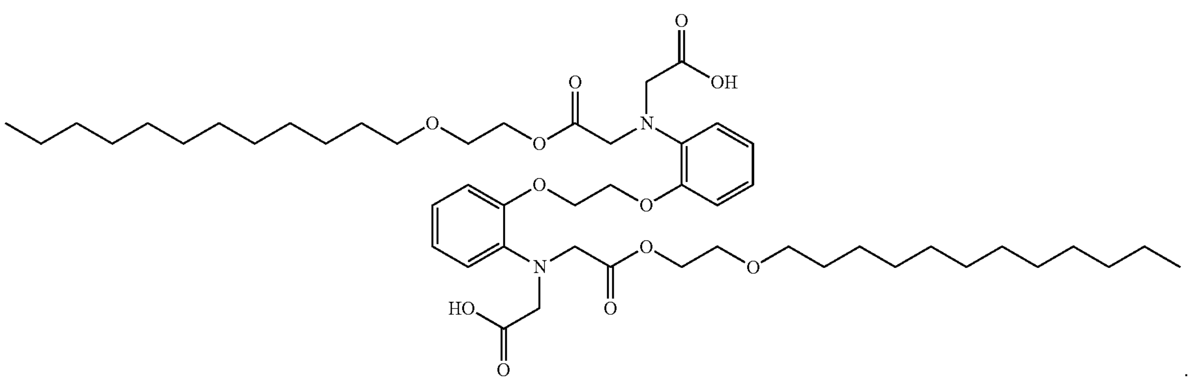

.

9. The method of claim 7, further comprising at least one or more other anti-parasitic compounds.

* * * * *